(12) United States Patent
Snyder et al.

(10) Patent No.: US 9,188,518 B2
(45) Date of Patent: Nov. 17, 2015

(54) GROUND COMPACTION IMAGES (71) Applicant: Bridgestone Americas Tire Operations, LLC, Nashville, TN (US)

(72) Inventors: Dennis W. Snyder, Uniontown, OH (US); Anthony B. Duncan, Wadsworth, OH (US)

(73) Assignee: Bridgestone Americas Tire Operations, LLC, Nashville, TN (US)

( * ) Notice: Subject to any disclaimer, the term of this patent is extended or adjusted under 35 U.S.C. 154(b) by 326 days.

(21) Appl. No.: 13/969,982

(22) Filed: Aug. 19, 2013

(65) Prior Publication Data

US 2015/0049088 A1    Feb. 19, 2015

(51) Int. Cl.
*G01M 17/02* (2006.01)
*G01N 3/06* (2006.01)

(52) U.S. Cl.
CPC .............. *G01N 3/062* (2013.01); *G01M 17/02* (2013.01); *G01N 2203/0019* (2013.01); *G01N 2203/0033* (2013.01); *G01N 2203/0087* (2013.01); *G01N 2203/0244* (2013.01); *G01N 2203/0284* (2013.01); *G01N 2203/0605* (2013.01)

(58) Field of Classification Search
None
See application file for complete search history.

(56) References Cited

U.S. PATENT DOCUMENTS

| | | | |
|---|---|---|---|
| 5,341,687 A | 8/1994 | Stan | |
| 5,347,588 A | 9/1994 | Wilson | |
| 6,032,522 A | 3/2000 | Clark et al. | |
| 6,546,791 B2 | 4/2003 | Yurjevich | |
| 6,736,004 B2* | 5/2004 | Evans | B60C 23/066 701/514 |
| 6,964,205 B2 | 11/2005 | Papakostas et al. | |
| 7,043,396 B2 | 5/2006 | Larson et al. | |
| 8,065,911 B2 | 11/2011 | Taylor et al. | |
| 2003/0055617 A1 | 3/2003 | Iwasaki et al. | |
| 2004/0107081 A1 | 6/2004 | Miyori et al. | |
| 2005/0194154 A1* | 9/2005 | Hester | E02D 3/026 172/1 |
| 2007/0195644 A1 | 8/2007 | Marples et al. | |
| 2007/0276602 A1 | 11/2007 | Anderegg et al. | |
| 2013/0124172 A1 | 5/2013 | Seta et al. | |
| 2013/0186194 A1 | 7/2013 | Schaefer | |
| 2014/0236431 A1* | 8/2014 | Hendrickson | A01B 9/005 701/50 |

FOREIGN PATENT DOCUMENTS

| | | |
|---|---|---|
| JP | 2005193825 A | 7/2005 |
| JP | 2005201851 A | 7/2005 |
| JP | 2005319942 A | 11/2005 |
| WO | 2012004413 A1 | 1/2012 |

OTHER PUBLICATIONS

International Search Report in corresponding International Application No. PCT/US2014/049003, dated Nov. 28, 2014, 3 pp. (not prior art).
Exhibit A: XSENSOR website printout of XSENSOR.com site (2 pages) (undated but admitted to be prior art).
Exhibit B: Tirescan System website printout of TEKSCAN.com site (13 pages) (undated but admitted to be prior art).

* cited by examiner

*Primary Examiner* — Andre Allen (57) ABSTRACT

A method is provided for generating a ground compaction image. A pressure sensing panel is placed on a relatively rigid planar supporting surface. The pressure sensing panel is covered with a depth of particulate material. A loaded tire is placed on the particulate material, and a ground compaction image is generated with the pressure sensing panel. A ground compaction display may be created by superimposing the ground compaction image on a physical three-dimensional model of an interface between the particulate material and the loaded tire.

28 Claims, 7 Drawing Sheets

GROUND COMPACTION IMAGES

BACKGROUND OF THE INVENTION

1. Field of the Invention

The present disclosure relates to methods of generating ground compaction images representative of the pressure distribution within the soil at a depth below a loaded tire, and to displays incorporating such ground compaction images.

2. Description of the Prior Art

It is known that the compaction of soil can be detrimental to the growth and development of plants which are planted in the soil. Excessive soil compaction can impede root growth and decrease the plants' ability to consume nutrients and moisture from the soil.

A major cause of soil compaction is the tires of tractors and other agricultural implements, and this problem increases as the agricultural equipment becomes larger and heavier.

One technique for reducing the amount of soil compaction due to wheeled traffic through a field is to reduce the tire pressure and thus spread the load over a larger footprint of the tire. Improved tire designs are being developed which are durable at these decreased inflation pressures.

To date, however, there has been no systematic technique available for demonstrating the soil compaction created by a given tire or to compare tire designs to determine or demonstrate the relative soil compaction performance of different tires.

SUMMARY OF THE INVENTION

In one aspect of the present disclosure a method is provided for generating a ground compaction image for a tire. The method comprises the steps of:

(a) placing a relatively flexible pressure sensing panel on a relatively rigid planar supporting surface;
(b) covering the pressure sensing panel with a depth of particulate material;
(c) placing a tire on the particulate material;
(d) loading the tire; and
(e) generating a ground compaction image with the pressure sensing panel.

In another embodiment of the present disclosure a ground compaction display for a tire comprises a physical three-dimensional model of an interface between a particulate material and a loaded tire, and a ground compaction image superimposed on the three-dimensional model.

In any of the above embodiments a perimeter container may be placed over the pressure sensing panel, and the perimeter container may be filled to the desired depth with the particulate material.

In any of the above embodiments the ground compaction image may be formed by first forming a depression in a ground surface and placing a supporting plate and the pressure sensing panel into the depression. The supporting plate has the supporting surface thereon. The particulate material is then placed into the depression on top of the panel.

In any of the above embodiments the depth of the particulate material may be in a range of from 2 inches to 12 inches.

In any of the above embodiments the particulate material may comprise sand, or soil, or mixtures thereof.

In any of the above embodiments the supporting surface may be defined on a flat plate.

In any of the above embodiments additional ground compaction images may be generated at different depths of particulate material.

In any of the above embodiments a three-dimensional representation of an interface between the loaded tire and the particulate material may be created, and then the ground compaction image may be superimposed on the three-dimensional representation.

In any of the above embodiments the three-dimensional representation may be created as a physical model. The physical model may be either a physical model of a depression formed in the particulate material by the loaded tire, or a physical model of at least that portion of the loaded tire contacting the particulate material.

The ground compaction image may be superimposed on the three-dimensional representation by any one of several techniques including: (1) printing the ground compaction image on the physical model; (2) projecting the ground compaction image on the physical model; (3) painting the ground compaction image on the physical model; (4) forming the ground compaction image into a surface of the physical model; or (5) forming the physical model with a 3d printer which also forms the ground compaction image integrally into the model.

In the methods of the present disclosure the three-dimensional representation may be created as a virtual three-dimensional image of either a depression formed in the particulate material by the loaded tire or that portion of the loaded tire contacting the particulate material.

In any of the above embodiments one or more additional three-dimensional models of an interface between the particulate material and another tire may be created, and a second ground compaction image may be superimposed upon the additional three-dimensional model, and the two three-dimensional models may be displayed adjacent each other so that an observer can compare the ground compaction images for two tires.

Numerous objects, features and advantages of the present invention will be readily apparent to those skilled in the art upon a reading of the following disclosure when taken in conjunction with the accompanying drawings.

DETAILED DESCRIPTION

A method is provided for generating a ground compaction image for a tire. By ground compaction image it is meant an image representative of the pressure distribution present within the soil at a depth below the interface of a loaded tire with the surface of the soil. This ground compaction image differs from a pressure footprint of the tire itself in that the pattern of such pressure dissipates and changes with increasing depth below the tire.

Figure 1A:
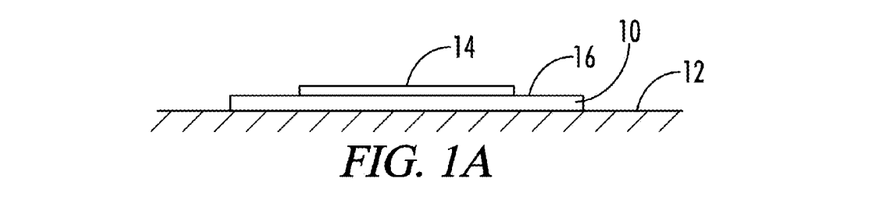
FIG. 1A is a schematic side elevation view of a pressure sensing panel in place on a supporting plate.

FIG. 1A is a side elevation view depicting certain components of a system that may be used to generate ground compaction images. In FIG. 1A a support plate 10 has been placed upon a floor 12, and a pressure sensing panel 14 has been placed on the support plate 10. In general, the pressure sensing panel 14 may be described as a relatively flexible, thin sheet like pressure sensing panel, and the supporting plate 10 has a top supporting surface 16 which may be described as a relatively rigid planar supporting surface 16. In the embodiment of FIG. 1A, it is also possible to eliminate the support plate 10 and place the pressure sensing panel 14 directly on the floor 12 in which case the floor 12 defines the relatively rigid planar supporting surface for the pressure sensing panel. Because of the relative flexibility of the panel 14, it is desirable to support the panel 14 with the relatively rigid planar supporting surface 16 in order to generate a pressure distribution image representative of that actually present at the selected depth below the ground surface. If the flexible panel 14 were merely buried in the ground it would deform and would not reliably generate the desired ground compaction images.

Figure 1B:
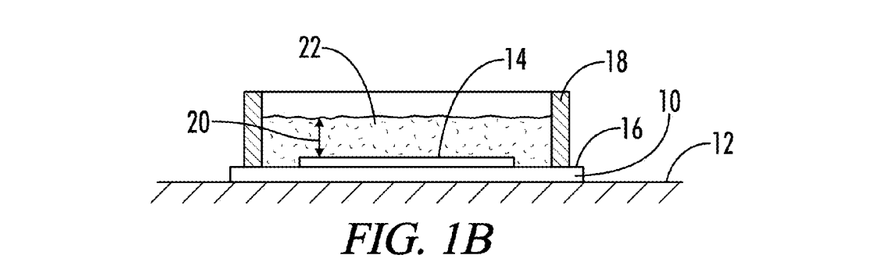
FIG. 1B is a schematic side elevation view of the apparatus of FIG. 1A with a perimeter container in place over the pressure sensing panel, and the container filled to the desired depth with particulate material.

In FIG. 1B, a perimeter container 18 has been placed over the pressure sensing panel 14 and the container 18 has been filled with particulate material 22 to a desired depth 20 over the pressure sensing panel 14.

Figure 1C:
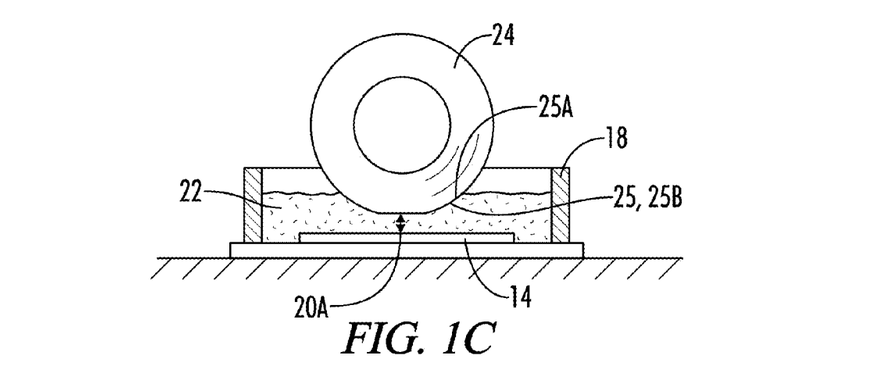
FIG. 1C is a schematic side elevation view of the apparatus of FIG. 1B with a tire having been placed on top of the fill of particulate material and loaded.

In FIG. 1C, a tire 24 has been placed on top of the particulate material 22 and the tire has been loaded to a desired load representative of the loading which will be placed on the tire in service. As seen in FIG. 1C, the tire has partially sunken into the particulate material to define an interface 25 between the tire 24 and the particulate material 22. The interface 25 can be represented by the shape of the depression 25A in the particulate material 22, or by the shape of that portion 25B of tire 24 which engages the particulate material 22. A lowermost portion of the tire is now separated from the pressure sensing panel 14 by a depth 20A which is less than the initial particulate depth 20.

In the configuration shown in FIG. 1C, the pressure sensing panel 14 can be utilized to generate a ground compaction image representative of soil compaction at a depth 20 below a ground surface.

Figure 1D:
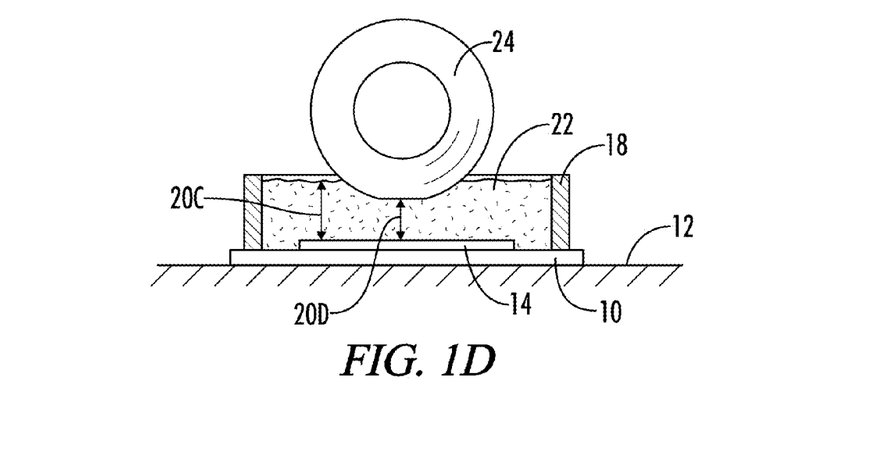
FIG. 1D is a schematic side elevation view similar to FIG. 1C, with the perimeter container having been filled with particulate material to a greater depth as compared to FIGS. 1B and 1C.

FIG. 1D shows the same apparatus of FIGS. 1A-1C, except that the particulate material was filled to a greater depth 20C prior to placement of the tire 24 on top of the particulate material, and now the lowermost portion of the tire 24 is located at an increased depth 20D above the pressure sensing panel 14. Thus the system depicted in FIG. 1D can be utilized to generate a ground compaction image representative of the compaction of the soil at a depth 20C below the ground surface.

Figure 2A:
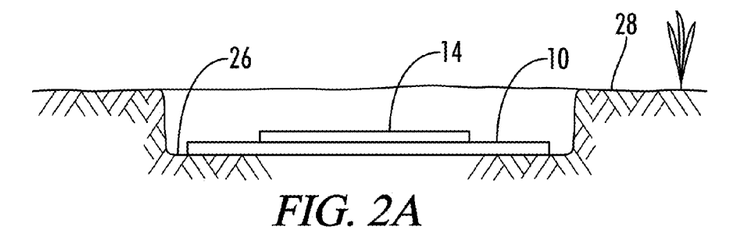
FIG. 2A is a schematic side elevation view of a depression formed in the ground surface, with the support plate and the pressure sensing panel having been placed in the depression.
Figure 2B:
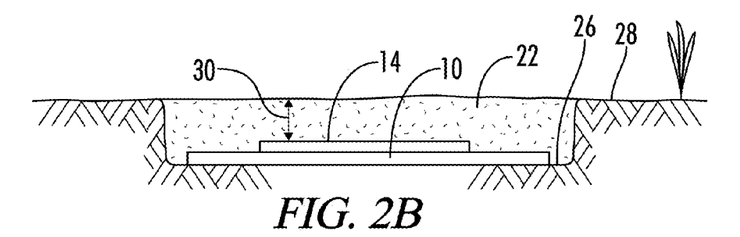
FIG. 2B is a schematic side elevation view of the apparatus of FIG. 2A, with the depression having been filled with particulate material.

FIGS. 2A-2D comprise a series of images similar to FIGS. 1A-1D, but for the situation where the supporting plate 10 and the pressure sensing panel 14 have been placed in a depression 26 formed in a ground surface 28. In FIG. 2B, the depression 26 has been filled with particulate material 22 to a depth 30 above the pressure sensing panel 14.

Figure 2C:
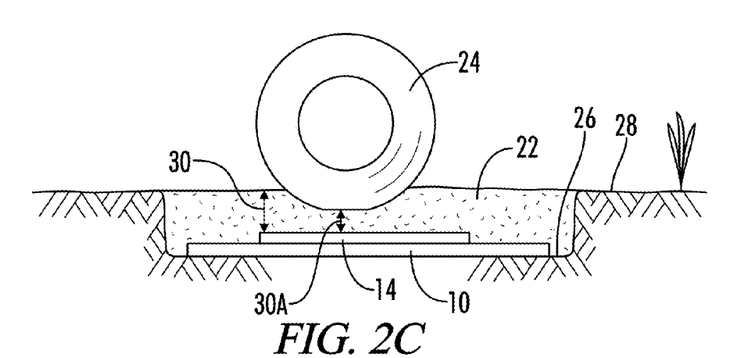
FIG. 2C is a schematic side elevation view of the apparatus of FIG. 2B with a loaded tire having been placed on top of the particulate fill.

In FIG. 2C the tire 24 has been placed on top of the ground surface and has been loaded so that it has sunken into the particulate material 22 and now the pressure sensing panel 14 may generate a ground compaction image representative of the compaction of the soil at a depth 30 below the ground surface 28 by the loaded tire 24. It is noted that the loaded tire 24 may be driven into place on top of the particulate material 22.

Figure 2D:
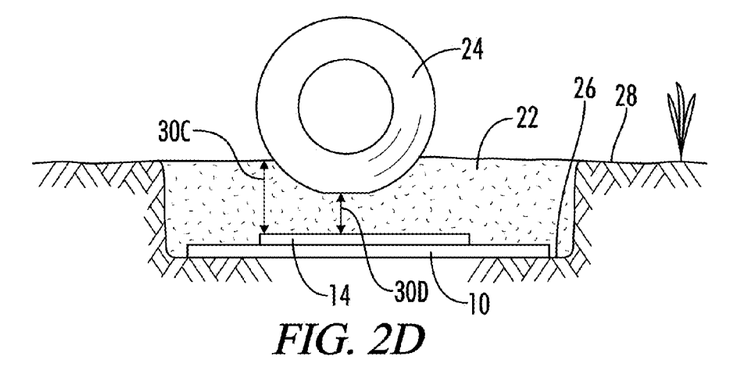
FIG. 2D is a schematic side elevation view similar to FIG. 2C, with the depression having been formed deeper and filled to a deeper depth with particulate material prior to the placement of the tire on top of the particulate fill.

FIG. 2D is a view similar to FIG. 2C, except in FIG. 2D the depression 26 has been formed at a greater depth, and the particulate material 22 has been filled to a greater depth 30C below the ground surface 28. In the arrangement of FIG. 2D, the pressure sensing panel can generate a ground compaction image representative of the soil compaction at a depth 30C below the ground surface 28 by the loaded tire 24.

With regard to soil compaction studies for agricultural purposes, the depth range of interest for the depth 20 shown in FIG. 1B or the depth 30 shown in FIG. 2B is preferably in a range of from about 2 inches to about 12 inches.

Figure 3:
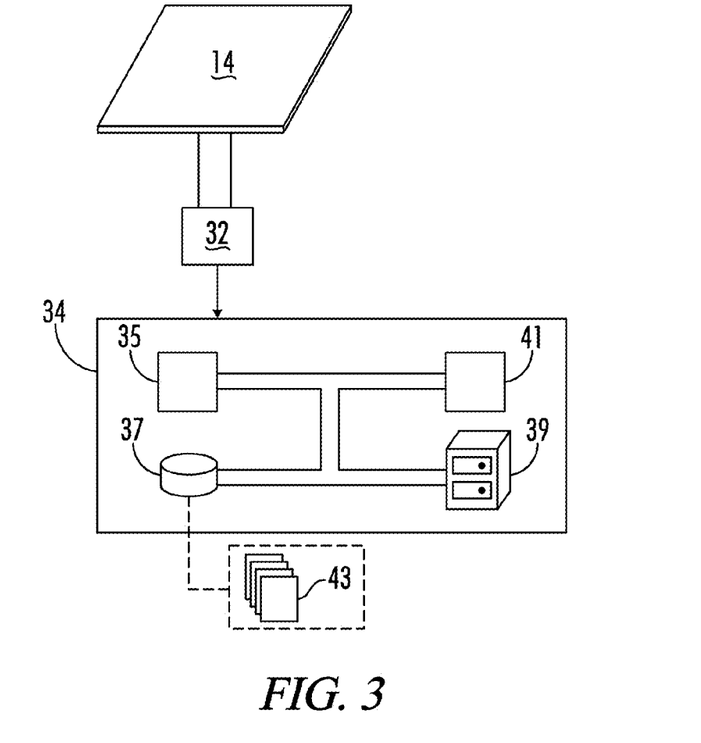
FIG. 3 is a schematic view of a pressure sensing panel, and a data collection system associated therewith for generating pressure prints corresponding to ground compaction images.

FIG. 3 is a schematic representation of the pressure sensing panel 14 and associated electronic equipment utilized therewith to generate the ground compaction image.

The pressure sensing panel 14 itself is an article which exists in the prior art and has previously been used for generating footprint images of tires. One available form of pressure sensing panel is that sold by Tekscan, Inc. of South Boston, Mass. as its TIRESCAN™ footprint pressure measurement system. Another available pressure sensing panel is that sold by XSensor Technology Corporation of Calgary, Alberta, Canada as its XSENSOR® X3 Tire Sensor System.

The pressure sensing panel 14 comprises an ultra-thin tactile pressure sensor system. Each panel has an array of individual sensing elements distributed across the area of the panel. The sensor density is related to the resolution of the images which can be generated by the panel.

A scanning electronics package 32 which is provided by the supplier of the pressure sensing panel 14 is utilized to gather data from the array of sensors in the panel and then process and send that sensor data to a computer system 34.

The computer system 34 is provided for receiving information from the sensors of panel 14, and for determining and saving data corresponding to the ground compaction images, and for communicating that data. FIG. 3 schematically illustrates the computer system 34 and its connection with the pressure sensing panel 14.

The computer system 34 further includes a processor 35, a computer-readable memory medium 37, a database 39 and an I/O platform or module 41 which may typically include a user interface generated by the program instructions in accordance with methods or steps described in greater detail below.

The term "computer-readable memory medium" as used herein may refer to any non-transitory medium 37 alone or as one of a plurality of non-transitory memory media 37 within which is embodied a computer program product 43 that includes processor-executable software, instructions or program modules which upon execution may provide data or otherwise cause a computer system to implement subject matter or otherwise operate in a specific manner as further defined herein. It may further be understood that more than one type of memory media may be used in combination to conduct processor-executable software, instructions or program modules from a first memory medium upon which the software, instructions or program modules initially reside to a processor for execution.

"Memory media" as generally used herein may further include without limitation transmission media and/or storage media. "Storage media" may refer in an equivalent manner to volatile and non-volatile, removable and non-removable media, including at least dynamic memory, application specific integrated circuits (ASIC), chip memory devices, optical or magnetic disk memory devices, flash memory devices, or any other medium which may be used to stored data in a processor-accessible manner, and may unless otherwise stated either reside on a single computing platform or be distributed across a plurality of such platforms. "Transmission media" may include any tangible media effective to permit processor-executable software, instructions or program modules residing on the media to be read and executed by a processor, including without limitation wire, cable, fiber-optic and wireless media such as is known in the art.

The term "processor" as used herein may refer to at least general-purpose or specific-purpose processing devices and/or logic as may be understood by one of skill in the art, including but not limited to single- or multithreading processors, central processors, parent processors, graphical processors, media processors, and the like.

The computer system 34 receives data from pressure sensing panel 14 and the scanning electronics package 32 corresponding to the ground compaction images. Then based upon programming 43 the system 34 generates the ground compaction images.

Figure 4A:
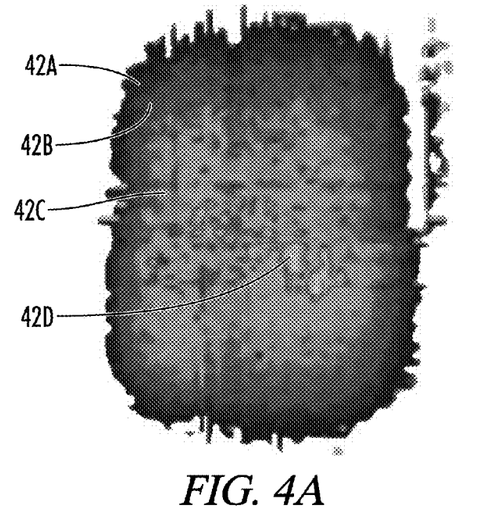
FIG. 4A depicts a ground compaction image for a 3 inch soil depth.
Figure 4B:
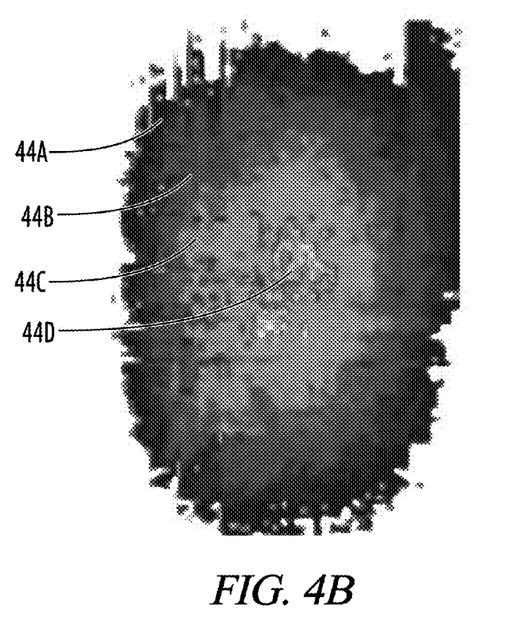
FIG. 4B depicts a ground compaction image for a 5 inch soil depth for the same tire as FIG. 4A.

FIGS. 4A and 4B show two examples of ground compaction images generated with the system of FIGS. 1-3. In this example upper ground compaction image 42 of FIG. 4A was generated using the system of FIGS. 1A-1D for a particulate depth 20 equal to 3 inches. The ground compaction image 44 of FIG. 4B was generated at a greater depth, in this case at a depth 20C of 5 inches.

Looking at the example of the ground compaction image 42 in FIG. 4A it includes an outer zone 42A, a first intermediate zone 42B, a second intermediate zone 42C, and a central zone 42D of varying colors or darkness which depict increasing pressures when moving from the outer portion 42A to the inner portion 42D. Although the images are shown in gray scale in FIGS. 4A and 4B, they would preferably utilize different colors for the various zones.

In comparing the similar colored areas 44A, 44B, 44C and 44D of the example 44 in FIG. 4B, it is seen that with greater depths, the pressures tend to decrease, such that the central areas of higher pressure shrink.

Thus, a method is provided by the systems of FIGS. 1-3 for generating ground compaction images like images 42 or 44 of FIG. 4, which method includes the steps of:
 (a) placing the relatively flexible pressure sensing panel 14 on a relatively rigid planar supporting surface such as the support plate 10 or the floor 12;
 (b) covering the pressure sensing panel with a depth of particulate material 22 such as the depth 20 shown in FIG. 1B or the depth 30 shown in FIG. 2B;
 (c) placing the tire 24 on the particulate material 22;
 (d) loading the tire 24; and
 (e) generating the ground compaction image such as 42 or 44 with the pressure sensing panel 14.

It is noted that steps (c) and (d) may be performed simultaneously by driving a loaded tire onto the particulate material.

If the method is performed on a floor or other supporting structure such as shown in FIG. 1A, the perimeter 18 shown in FIGS. 1B and 1C may be utilized to contain the particulate material in place over the pressure sensing panel 14.

If the pressure sensing panel is to be placed in a depression in the ground as shown in FIGS. 2A-2B, then the depression in the ground is formed and the supporting plate 10 is placed in the depression with the panel placed on top of the supporting plate, and then the depression is filled with the particulate material 22.

In addition to creating the ground compaction images, the present disclosure provides numerous techniques for displaying those images so that an observer can appreciate the relative ground compaction performance of various tires.

One technique for displaying the ground compaction images is to create a three-dimensional representation of the interface 25 between the loaded tire 24 and the particulate material 22. It will be appreciated that the three-dimensional representation of the interface can either be in the form of a three-dimensional representation of the depression 25A formed in the particulate material by the loaded tire, or a three-dimensional representation of at least that portion 25B of the loaded tire which contacts the particulate material.

Additionally, the three-dimensional representation may be created as a physical model, or in some situations a virtual model may be generated for display purposes.

Figure 5:
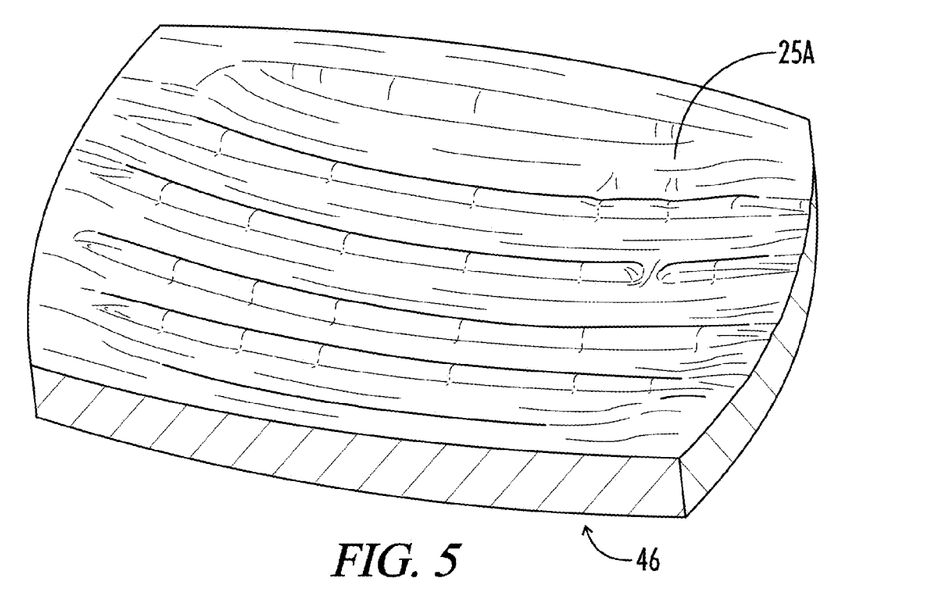
FIG. 5 is a perspective view of a physical model of a three-dimensional representation of the interface between a loaded tire and the particulate material, wherein the physical model is a model of the depression formed in the ground surface by the loaded tire.

FIG. 5 illustrates a physical model 46 of a depression formed in the particulate material by the loaded tire.

Figure 7:
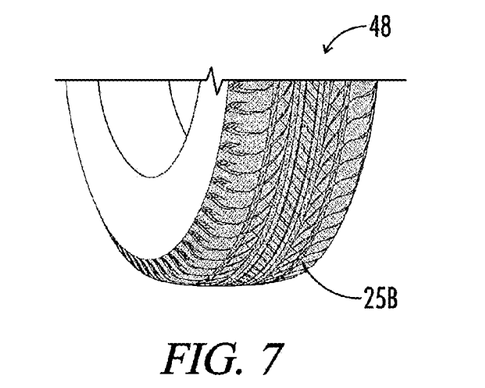
FIG. 7 is a schematic perspective view of a three-dimensional physical model including that portion of a loaded tire contacting the ground surface or the particulate material.

FIG. 7 illustrates a physical model 48 of a loaded tire including at least that portion of the loaded tire contacting the particulate material.

Figure 6:
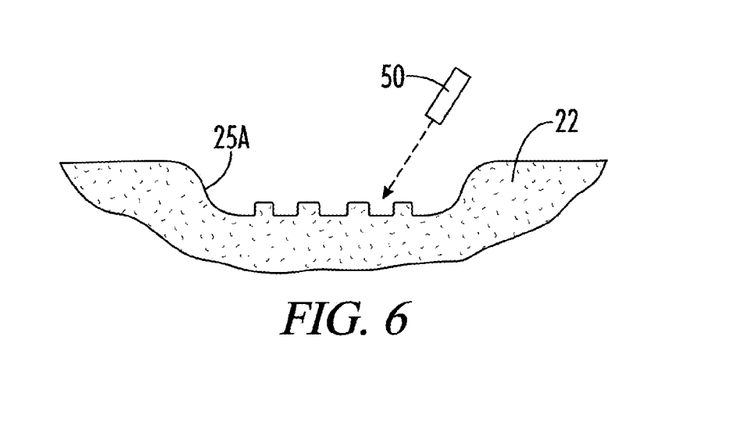
FIG. 6 is a schematic representation of a technique for generating the physical model of FIG. 5, wherein the depression in the particulate material is scanned with a laser scanner to generate a three-dimensional profile which can be reproduced in a three-dimensional printer.

FIG. 6 schematically illustrates one technique for generating the physical model 46 of FIG. 5. As shown in FIG. 6, the loaded tire 24 has been removed from the particulate filled container 18 of FIG. 1C thus leaving the recess 25A as formed in the particulate material 22. A laser scanning device 50 is then utilized to scan the three-dimensional profile of the recess 25A. Then using the three-dimensional profile created by the laser scanning device 50, the physical model 46 may be formed by three-dimensional printing or other techniques for reproducing the three-dimensional object from the digital file defining the profile of the recess 25A.

One particularly desirable technique for displaying the ground compaction images such as 42 and 44 and for associating those images in the viewer's mind with the particular tire design being demonstrated, is to superimpose the ground compaction image on a physical model such as model 46 or 48.

Figure 8:
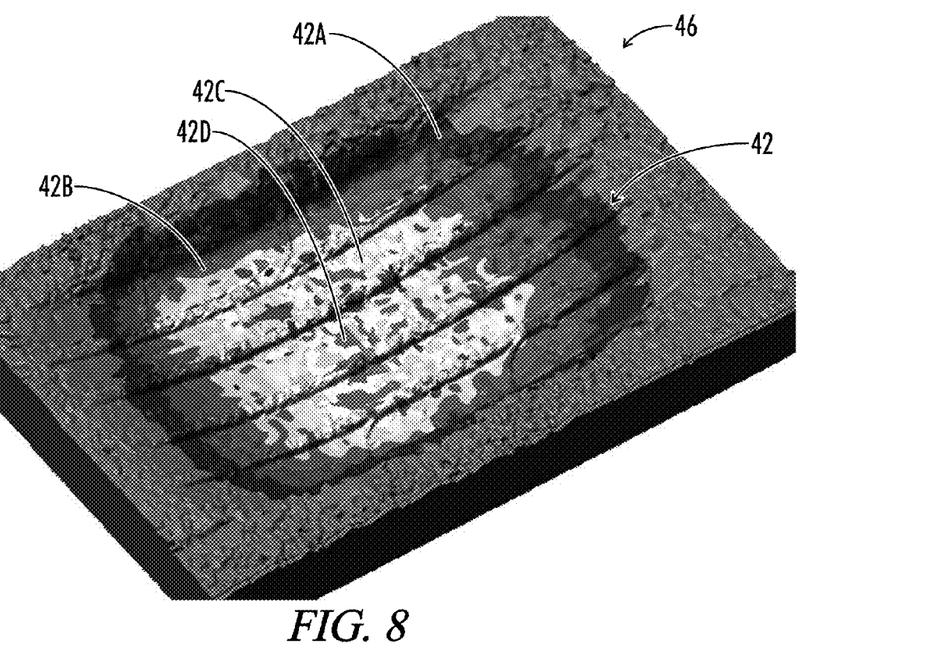
FIG. 8 is a schematic perspective view of the three-dimensional physical model of FIG. 5 with a ground compaction image superimposed thereon.

FIG. 8 schematically illustrates the physical model 46 of FIG. 5 with the ground compaction image 42 of FIG. 4 superimposed thereon.

It is noted, that the particular ground compaction image selected for display on the physical model 46 will typically be the ground compaction image representative of the pressure distribution at a distance slightly below the interface 25, and it is not necessary that the ground compaction image displayed on the physical model correspond exactly to the pressure distribution directly at the interface 25. The display technique illustrated in FIG. 8 is merely a technique for combining a three-dimensional representation of the interface 25 with an associated ground compaction image of any selected depth to correlate in the viewer's mind the relationship between the tire design and the ground compaction image which has been provided.

The ground compaction images may be superimposed upon the physical model in various ways.

The ground compaction image may be printed on the physical model by any of available printing technique.

The ground compaction image may be projected on the physical model with a projector. When using a projector, the projector could sequentially project different ground compaction images on the physical model.

The ground compaction image may be painted on the physical model.

The ground compaction image may be formed into the surface of the physical model by molding, engraving, machining or any other available technique.

The ground compaction image may be integrally formed on the physical model by manufacturing the physical model with a 3D color printer which can create the colored ground compaction image as part of the 3d model from a data file including information describing both the physical model and the ground compaction image.

If the three-dimensional representation of the interface is a virtual representation, then the ground compaction image may be superimposed upon the three-dimensional image via digital techniques.

Figure 9:
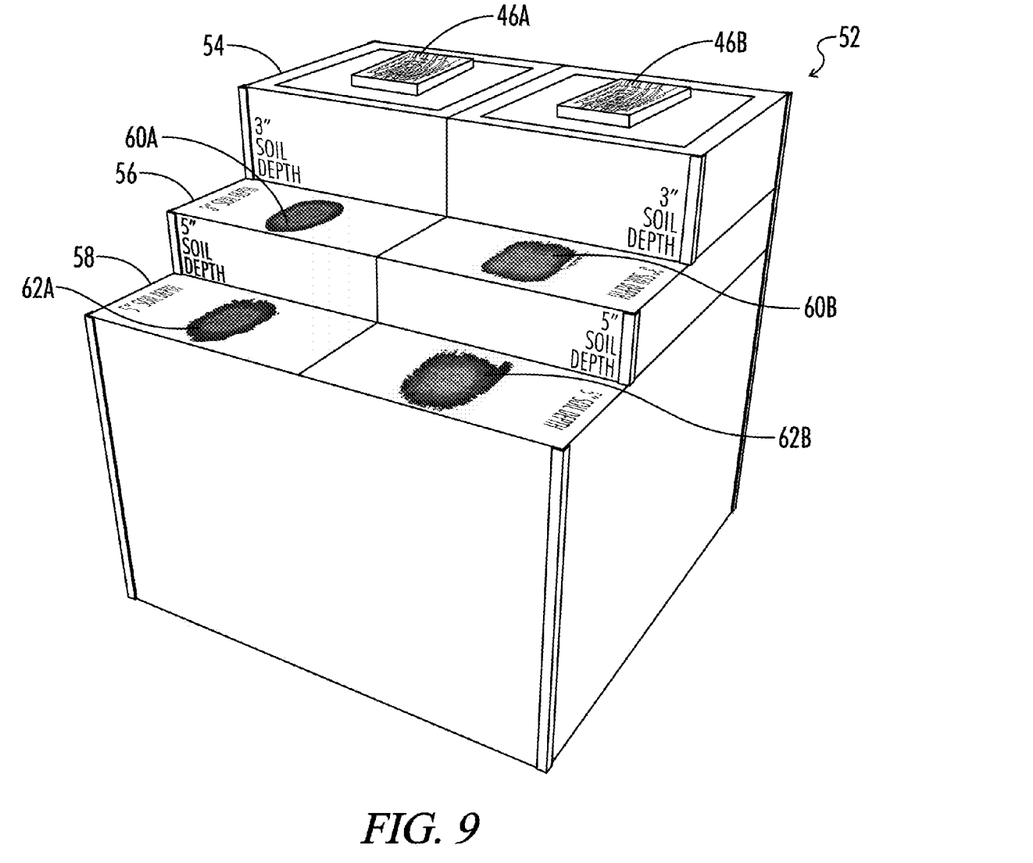
FIG. 9 is a schematic perspective view of a display comparing the ground compaction images of two tires. On the left hand side of the display at the top is a three-dimensional model such as that of FIG. 5 or 7 having a ground compaction image at a relatively shallow depth, superimposed on the three-dimensional model. The intermediate and lower steps display additional ground compaction images taken at greater depths such as 3 inches and 5 inches.

Additionally, the display may include side-by-side displays of ground compaction images generated for different tires which are to be compared. For example, in FIG. 9 a display 52 has an upper display surface 54 on which are displayed two three-dimensional representations of the recess formed in the ground, similar to the display of FIG. 8, which displays are designated as 46A and 46B. The displays 46A and 46B may have a ground compaction image superimposed thereon in the manner illustrated in FIG. 8, or they may simply be a physical representation of the depression 25A as shown in FIG. 5. The display includes intermediate and lower display surfaces 56 and 58 on which are displayed side by side ground compaction images 60A and 60B taken at a first depth, for example 3 inches, and ground compaction images 62A and 62B taken at a second depth, for example 5 inches.

Thus it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A method of generating a ground compaction image for a tire, comprising:
   (a) placing a relatively flexible pressure sensing panel on a relatively rigid planar supporting surface;
   (b) covering the pressure sensing panel with a depth of particulate material;
   (c) placing a tire on the particulate material;
   (d) loading the tire; and
   (e) generating a ground compaction image with the pressure sensing panel.

2. The method of claim 1, wherein:
   step (b) further comprises placing a perimeter container over the pressure sensing panel, and filling the container to the depth with the particulate material.

3. The method of claim 1, wherein:
   step (a) further comprises forming a depression in a ground surface and placing a supporting plate and the panel into the depression, the supporting plate having the supporting surface defined thereon; and
   step (b) further comprises placing the particulate material into the depression on top of the panel.

4. The method of claim 1, wherein:
   in step (b) the depth is in a range of from 2 inches to 12 inches.

5. The method of claim 1, wherein:
   in step (b) the particulate material comprises sand.

6. The method of claim 1, wherein:
   in step (b) the particulate matter comprises soil.

7. The method of claim 1, wherein:
   in step (a) the supporting surface is defined on a flat plate.

8. The method of claim 1, further comprising:
   repeating steps (b)-(e) for one or more different depths of particulate material.

9. The method of claim 1, further comprising:
   creating a three-dimensional representation of an interface between the loaded tire and the particulate material; and
   superimposing the ground compaction image on the three-dimensional representation.

10. The method of claim 9, wherein:
    the creating step comprises creating a physical model comprising the three-dimensional representation.

11. The method of claim 10, wherein:
    in the creating step the physical model comprises a physical model of a depression formed in the particulate material by the loaded tire.

12. The method of claim 10, wherein:
    in the creating step the physical model comprises a physical model of at least that portion of the loaded tire contacting the particulate material.

13. The method of claim 10, wherein:
    the superimposing step comprises printing the ground compaction image on the physical model.

14. The method of claim 10, wherein:
    the superimposing step comprises projecting the ground compaction image on the physical model.

15. The method of claim 10, wherein:
    the superimposing step comprises painting the ground compaction image on the physical model.

16. The method of claim 10, wherein:
    the superimposing step comprises forming the ground compaction image into a surface of the physical model.

17. The method of claim 10, wherein:
the superimposing step comprises printing the physical model in a 3D color printer and creating the ground compaction image as a part of the physical model.

18. The method of claim 9, wherein:
the creating step comprises creating a virtual three-dimensional image of a depression formed in the particulate material by the loaded tire.

19. The method of claim 9, wherein:
the creating step comprises creating a virtual three-dimensional image of that portion of the loaded tire contacting the particulate material.

20. A ground compaction display for a tire, comprising:
a physical three-dimensional model of an interface between a ground surface and a loaded tire; and
a ground compaction image superimposed on the three-dimensional model.

21. The display of claim 20, wherein:
the physical three-dimensional model comprises a model of a depression formed in the ground surface by the loaded tire.

22. The display of claim 20, wherein:
the physical three-dimensional model comprises a model of at least that portion of the loaded tire contacting the ground surface.

23. The display of claim 20, wherein:
the ground compaction image is printed on the physical model.

24. The display of claim 20, wherein:
the ground compaction image is projected on the physical model.

25. The display of claim 20, wherein:
the ground compaction image is painted on the physical model.

26. The display of claim 20, wherein:
the ground compaction image is formed into a surface of the physical model.

27. The display of claim 20, wherein:
the ground compaction image is integrally formed on the physical model by a 3d color printer.

28. The display of claim 20, further comprising:
a second three-dimensional model of an interface between a ground surface and a second tire, and a second ground compaction image superimposed on the second three-dimensional model; and
wherein the first and second three-dimensional models are located adjacent each other such that an observer can compare the ground compaction images for the two tires.

* * * * *